United States Patent [19]

Lee et al.

[11] Patent Number: 4,749,653

[45] Date of Patent: Jun. 7, 1988

[54] ENZYME IMMOBILIZATION ON NON-POROUS GLASS FIBERS

[75] Inventors: David M. Lee, Newark; Gary M. Nishioka, Pataskala, both of Ohio; Wayne E. Swann, Columbia; Carol A. Nolf, Silver Spring, both of Md.

[73] Assignee: Owens-Corning Fiberglas Corporation, Toledo, Ohio

[21] Appl. No.: 789,530

[22] Filed: Oct. 21, 1985

[51] Int. Cl.$^4$ .................. C12N 11/14; C12N 11/02; C12N 11/08

[52] U.S. Cl. .................. 435/176; 435/177; 435/180

[58] Field of Search .............. 435/174, 176, 177, 180, 435/182; 530/811, 825

[56] References Cited

U.S. PATENT DOCUMENTS

| | | | |
|---|---|---|---|
| 3,669,841 | 6/1972 | Miller | 435/176 |
| 3,715,278 | 2/1973 | Miller | 435/176 X |
| 3,806,412 | 4/1974 | Gagne et al. | 195/176 X |
| 3,983,000 | 9/1976 | Messing et al. | 435/176 |
| 3,985,617 | 10/1976 | Yugari et al. | 435/180 |
| 4,071,339 | 1/1978 | Griffiths | 65/3.1 |
| 4,121,974 | 10/1978 | Hofreiter et al. | 435/176 X |
| 4,204,040 | 5/1980 | Keyes | 435/176 |
| 4,210,722 | 7/1980 | Silver | 435/176 |
| 4,217,415 | 8/1980 | Barabino et al. | 435/176 X |
| 4,229,536 | 10/1980 | DeFilippi | 435/176 |
| 4,230,803 | 10/1980 | Weidenbach et al. | 435/176 |
| 4,248,969 | 2/1981 | Lee | 435/176 |
| 4,266,029 | 5/1981 | Branner-Jorgensen | 435/176 |
| 4,268,419 | 5/1981 | Rohrbach | 435/176 X |
| 4,268,423 | 5/1981 | Rohrbach | 435/176 X |
| 4,287,305 | 9/1981 | Compere et al. | 435/176 |
| 4,323,650 | 4/1982 | Rosevear | 435/176 X |
| 4,337,172 | 6/1982 | Teague et al. | 435/176 |
| 4,415,663 | 11/1983 | Symon et al. | 435/176 |
| 4,415,664 | 11/1983 | Barszcz et al. | 435/176 |
| 4,416,992 | 11/1983 | Arena et al. | 435/176 |
| 4,434,228 | 2/1984 | Swann | 435/180 X |
| 4,504,582 | 3/1985 | Swann | 435/176 X |
| 4,525,457 | 6/1985 | Sakata | 435/178 |

FOREIGN PATENT DOCUMENTS 1491261 11/1977 United Kingdom .

OTHER PUBLICATIONS

"Immobilization of Glucoamylase from *Aspergillus niger* on Poly(Ethylenimine)-coated Non-Porous Glass Beads", by B. P. Wasserman et al. Enzyme Microb. Technol, vol. 4, 1982, pp. 107–109.

"Immobilization of Glucoamylase on Porous Silicas", by O. V. Lomako et al. Enzyme Microb. Technol. vol. 4, 1982, pp. 89–92.

*Primary Examiner*—David M. Naff

*Attorney, Agent, or Firm*—Patrick P. Pacella; Robert F. Rywalski

[57] ABSTRACT

Enzymes are immobilized on non-porous glass fibers by coating glass fibers with a solution containing an enzyme and a soluble polymer and contacting the coated fibers with a controlled amount of cross-linking agent to obtain an immobilized enzyme having high activity and long endurance, and which provides a high percentage of conversion. The enzyme may be an amylase, the polymer a plyalkyleneimine and the cross-linking agent glutaraldehyde. Continuous immobilization can be carried out by moving continuous fibers to applicator stations for applying a solution of enzyme and polymer and a solution of cross-linking agent.

26 Claims, 2 Drawing Sheets

ENZYME IMMOBILIZATION ON NON-POROUS GLASS FIBERS

FIELD OF THE INVENTION

The present invention relates to immobilization of enzymes and particularly to the immobilization of glucomylase and other enzymes on glass fibers.

BACKGROUND OF THE INVENTION

Enzymes are proteins which catalyze chemical reactions. Their actions generally are quite specific. For example, glucoamylase is an enzyme which catalyzes the saccharification of a starch hydrolyzate, the enzyme substrate, to glucose (dextrose), the end product. Glucose is widely used in the manufacture of fructose from starch.

Fructose is an isomer of dextrose that is sweeter than dextrose, and, therefore, it is widely used as a sweetener. In the manufacture of fructose, starch, e.g., corn starch, is hydrolyzed by acid or enzyme thinning to a dextrose equivalent (D.E.) of, e.g., 10, and then subject to enzymatic saccharification with glucoamylase to produce a product having a D.E. above 95, preferably as high as possible. The product, which can be called dextrose, is isomerized with glucose isomerase to produce fructose.

In conventional technology, glucoamylase is used on a batch basis to react with starch hydrolysis products. At the end of the reaction, as in many enzymatic reactions, it is difficult to recover the glucoamylase, and therefore a fresh supply must be used for each batch. As in the case of many enzymatic reaction, it has been recognized that this expense can be avoided if the glucoamylase can be immobilized on a support that is contacted with the starch hydrolyzate and then recovered. However, attempts to immobilize glycoamylase on porous supports in the past have failed to yield an enzyme capable of converting available starch to sugar at rates comparable to the free enzyme.

In order for an enzyme to be immobilized on a support and function in a satisfactory manner, certain requirements must be satisfied. First, the efficiency of the enzymatic reaction should not be diminished to any significant degree. Second, the supported enzyme must be durable, so that it will preserve its activity through several reactions. Third, the cost of immobilizing the enzyme must be reasonable, so that the overall cost of conducting the enzymatic reaction is not increased, and preferably is significantly reduced.

Many attempts to immobilize enzymes on solid supports have involved the use of porous supports. Porous supports are selected because they have large surface areas in proportion to the volume of the support (the surface area:volume ratio is high). For example, controlled pore glass has been described extensively in the literature as a support for enzymes. However, the diameters of the pores in such supports generally are small, and therefore it may be difficult for large molecules such as starch hydrolyzate to penetrate them. On the other hand, non-porous supports, which do not have this difficulty, have relatively low surface area:volume ratios, and therefore enzymes immobilized on them have relatively low activity.

Controlled pore glass also is quite expensive. Therefore, the potential cost advantages of immobilization of enzymes may not be achieved when it is used, especially with relatively inexpensive enzymes. While less expensive porous supports such as alumina also have been described in the literature, they nevertheless suffer from the other disadvantages described above.

U.S. Pat. No. 3,715,278 discloses the use of glass, in the form fibers or fabrics, as a support for enzymes, but does not disclose how to compensate for the relatively low surface area of glass.

U.S. Pat. No. 4,434,228 discloses the use of polymers of polyalkyleneimines and polycarboxylic acid which are mixed with enzymes to form particles. Post treatment with cross-linking agents is disclosed.

An immobilized enzyme composite and a method for immobilizing the enzyme on a bundle of non-porous filaments, such as glass, have now been discovered which provide an enzyme capable of retaining a high level of activity, an enzyme having long endurance and an enzyme which achieves a significantly high rate of conversion of enzyme substrate to the corresponding end product. Such an immobilized enzyme product will be particularly suited for commercial and biomedical processes utilizing enzyme catalysis, especially since the present invention overcomes the expense and inefficiencies of enzyme reactions conducted on a batch basis, as known in the past.

OBJECTS OF THE INVENTION

The objects of the present invention are to provide immobilized enzymes, particularly glucoamylase, which are inexpensive to manufacture, durable in use and provide high activity and rate of enzyme substrate conversion to end product.

SUMMARY OF THE INVENTION

The present invention provides an enzyme which is immobilized on a non-porous support, particularly filaments or fibers, and especially glass filaments. The enzyme is embedded in a matrix coated on the exterior of the glass fibers. The matrix is comprised of a polymer which has been insolubilized by cross-linking and whose degree of cross-linking is controlled to permit penetration by the enzyme substrate which is to react with the enzyme. The agent which cross-links the polymer may also link the enzyme to the polymer so as to immobilize it within the matrix. The preferred polymer is polyethyleneimine which has amine and imine groups susceptible to cross-linking.

An important feature of the invention is the control of the degree of cross-linking by controlling the amount of cross-linking agent applied. It has been found that the activity of the immobilized enzyme can be reduced excessively if too much cross-linking agent is applied. On the other hand, if the amount of cross-linking agent is too low, the enzyme's endurance is reduced. By a proper selection of the amount of cross-linking agent applied, it is possible to achieve a balance of high enzyme activity and long endurance, while achieving a high percentage of conversion of enzyme substrate to the end product.

The invention also provides a process for applying the enzyme to filaments or fibers which comprises applying a liquid composition which contains both the enzyme and the polymer, and subsequently applying a cross-linking agent. The amount of cross-linking agent is carefully controlled, either by controlling the concentration in a solution or by carefully metered application rate, so as to regulate the amount of cross-linking. In accordance with a preferred form of the invention, the fibers of filaments are in the form of a continuous bundle which is moved past two applicator stations. Carefully metered quantities of solutions are applied to the bundle as it passes these stations. At the first station, a liquid which contains the polymer and enzyme is applied. A solution of the cross-linking agent is applied at the second station. The bundle is then wound onto a takeup roll. In one form of the invention, the bundle is not wound up until a time period has passed after leaving the second applicator station. This delay may be accomplished by passing the bundle over a series of rolls or by other means, known per se in the handling of textiles.

DETAILED DESCRIPTION OF PREFERRED EMBODIMENT

The present invention provides an immobilized enzyme composite comprising a bundle of non-porous fibers or filaments, especially glass filaments, and an enzyme-containing composition, covering at least a portion of the surfaces of the filaments, which is the residue derived by drying a liquid chemical composition. The liquid chemical composition is one comprising an enzyme coating system, which contains the enzyme and a polymer, and a solution of a cross-linking agent. The enzyme-containing composition covering the fibers forms a matrix of a polymer which has been insolubilized through cross-linking. The degree of cross-linking is controlled so as to permit penetration by the enzyme substrate which is reactive with the enzyme. Without being limited as to theory, it is believed that the cross-linking agent may also link the enzyme to the polymer, thereby immobilizing it within the matrix.

Figure 1:
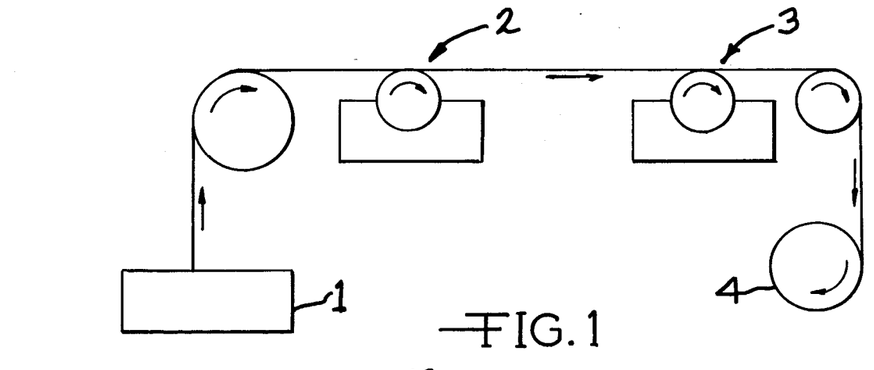
FIG. 1 is a schematic view of a continuous process for immobilizing an enzyme on glass fibers.
Figure 2:
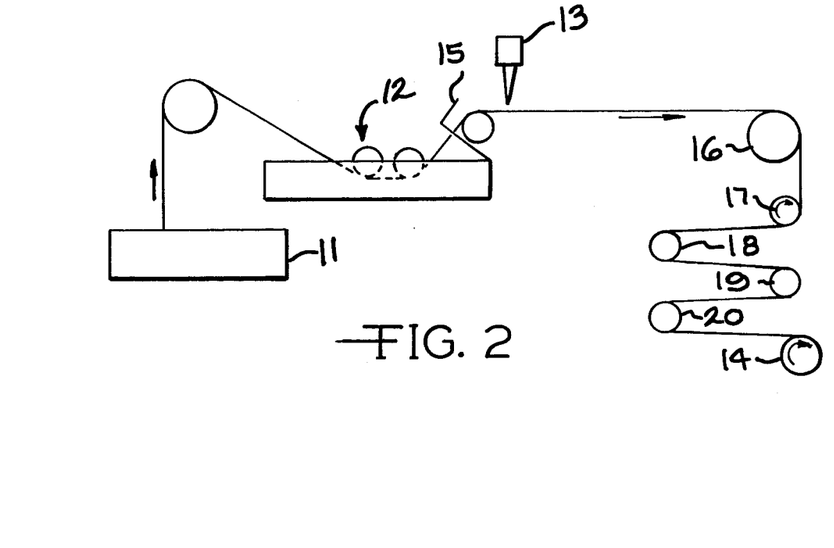
FIG. 2 is a schematic view of another embodiment of the process for immobilizing an enzyme on glass fibers.

The process for applying the liquid chemical composition, i.e., the enzyme coating system and the cross-linking agent, to non-porous filaments, is shown in FIGS. 1 and 2.

In the embodiment illustrated in FIG. 1, a bundle of glass filaments 1 is fed by rollers, not shown, to an enzyme application station 2 where it is coated with a solution of a polymer which has the enzyme dispersed in it. A metered quantity of the solution is applied to a roller at that station, and thus to the glass filaments as they come into contact with the roller. The filaments are then fed to another station 3 where they contact a roll which applies a metered quantity of an aqueous solution of the cross-linking agent. Then the filaments are collected on a windup roll 4.

In the embodiment illustrated in FIG. 2, the bundle of glass filaments 11 supplies filaments through rollers, not shown, to an enzyme application station 12 where they are immersed in a solution containing the enzyme. Then the filaments are passed through a stripper die 15 which removes solution in excess of a desired pickup. The filaments then are treated with cross-linking agent by means of a metering pump at station 13. Next, the filaments are festooned over rolls 16, 17, 18, 19 and 20, and wound on a takeup roll 14.

The filaments used in the present invention are preferably composed of glass. A preferred type of glass for use in the glass filaments is E-glass which is an alkali-borosilicate glass having the following composition: $SiO_2$, 34%; $Al_2O_3$, 14.2%; $B_2O_3$, 8.6%; $Na_2O$, 0.8%; $CaO$, 19.5%; $MgO$, 3.1%. S glass, which is a magnesia-alumina-silicate glass may also be used, although E-glass is less expensive and adequately durable. Also useful are the aramid (polyphenylene terephthalamide) filaments sold by E. I. duPont under the name Kevlar ®. Fialments of a relatively wide range of diameters may be used, although, in general, smaller diameters are preferred so as to increase the surface area:volume ratio. Diameters of 3 to 20 microns are preferred. The filaments are normally used in a bundle which contains 10 to 1,000 filaments. The bundles may be formed into yarns, cords, mats, fabrics, and the like. While continuous filaments are preferred, rovings or the like made from staple fibers also are useful.

The glass fibers may be sized with conventional glass fiber sizing compositions or coated with the polymer of the enzyme coating system of the instant invention, prior to immobilizing the enzymes on the fibers. However, good results have been obtained with glass filaments which have not been sized or pretreated.

The solution applied at the enzyme station, the enzyme coating system, is one comprising the polymer and an enzyme, as well as other components.

The polymer is one which includes groups which are reactive with the cross-linking agent so that it can be insolubilized through cross-linking. Preferred polymers are the polyalkyleneimines, which include polyethyleneimines, polypropyleneimines, polybutyleneimines and polypentyleneimines. Most preferred is polyethyleneimine, having a molecular weight of at least 35,000–40,000. Entirely satisfactory results have been achieved with the polyethyleneimine of BASF Wyandotte, Wyandotte, Mich., U.S.A., known as Polymin P, which has a molecular weight of 50,000–60,000 and is supplied as a solution in water containing 50% polymer.

A variety of enzymes are suitable in the present invention, especially those which contain a group capable of reacting with the cross-linking agent. For example, useful enzymes may have an amino group which is capable of reacting with an aldehyde or an isocyanate so as to be cross-linked with itself and/or the polymer. Included within this category is a wide variety of enzymes which may be included within the following categories: hydrolytic enzymes, redox enzymes, transferase enzymes, proteolytic enzymes, proteases, amylases, lipases, cellulases, carbohydrases, esterases, nucleases, hydrolases, hydrases, oxidoreductases, demolases, isomerases, alkaline and acid phosphatases and amidases. Included within these categories are the following representative enzymes which may be used with the present invention: papain, pepsin, trypsin, chymotrypsin, bromelain, keratinase, maltase, pectinase, chitinase, cholinesterase, lecithinase, ribonuclease, desoxyribonuclease, arginase, asparginase, glutaminase, urease, glucose oxidase, catalase, peroxidase, liporidase, cytochrome reductase, glutamicoxalacetic transaminase, transmethylase, phosphopyruvic transphosphorylase, rennin, carboxypepsidase, glucose isomerase, alpha amylase, beta amylase, gamma amylase, amylglucoxidase, invertase, galactase, xylose isomerase, beta-galactosidase, lactase, urease, urokinase, amino acid acylase, aspartase, keritinase, maltase, pectinase, chitinase, glutaminase, histidase, lactate dehydrogenase, invertase, alcohol dehydrogenase, collagenase, pepsin-pepsinogen, aminopeptidase, trypsin-trypsinogen, hemicellulase and cholesterol oxidase.

Particularly useful enzymes will be the amylases, especially glucoamylase. Satisfactory results have been obtained with Diazyme ® L-200, a glycoamylase solution supplied by Miles Laboratories, Inc., Elkhart, Ind., U.S.A., which has a concentration of about 35% solids in water suspension, contains 1-2% glucose and has an activity of about 35,000 units/gram of dry weight measure at pH 4.0 at 60° C. after ½ hour in 10 wt%, 10 D.E. maltodextrin solution. One unit of activity as used herein, is the amount of enzyme that will produce one micromole of end product, such as glucose, per minute.

The enzyme coating system, which contains the polymer and the enzyme, may be an aqueous or non-aqueous solution. Any non-aqueous or organic solvent is suitable in which the polymer exhibits good solubility and which does not denature the enzyme, such as acetone. After coating the glass bundle with a non-aqueous enzyme-polymer solution, it may be necessary to dry the coating before applying the cross-linking agent. Preferably, an aqueous solution of enzyme and polymer is employed.

The cross-linking agent is preferably a dialdehyde containing 1-10 carbon atoms in addition to the carbon atoms in the aldehyde groups, especially dialdehydes containing 3-6 carbon atoms. Glutaraldehyde has been found to be especially useful. In addition, polyisocyanates have been found useful, especially aromatic polyisocyanates. Examples of suitable polyisocyanates include toluene diisocyanates, methylene bis(phenyl-4-isocyanate) and poly-phenylene-polymethylene polyisocyanates. Other useful cross-linking agents include difunctional alkyl and acyl halides, divinyl sulfones and oxiranes, particularly ethylene oxide.

In addition to the foregoing, other components may be incorporated in the treatment solutions which improve the activity or durability of the immobilized enzyme.

Additions which have been found useful for the enzyme coating system include substrate for the enzyme. In the case of glucoamylase, a hydrolyzed starch or maltodextrin, which has a dextrose equivalent (D.E.) of about 10, is useful. Maltodextrin increases the viscosity of the solution and therefore increases the thickness of coatings which are obtained. It also is thought to "lock in" the preferred conformation of glucoamylase.

The amount of substrate added must be limited; excessive amounts may actually reduce the activity of the immobilized enzyme. When immobilizing glucoamylase, it is desirable that maltodextrin comprise from about 1% to about 5% by weight of the enzyme coating system. The maximum desirable amount of maltodextrin is about 5% by weight of the enzyme coating solution when immobilizing glucoamylase.

In addition, it is desirable to include a thickener which increases the amount of enzyme and polymer which is applied to the filaments in a single pass. A suitable material is hydroxyethyl cellulose (Natrosol 250HR, a non-ionic water-soluble cellulose ether that typically yields a solution viscosity of 1500-2500 centipoise at 30° C. using a Brookfield LOF viscometer with a #3 Spindle at 30 RPM). Also, in the case of glucoamylase, a small amount of calcium chloride has been found helpful. Adding from about 0.02% to about 0.06% calcium chloride by weight, especially 0.04% calcium chloride, to the enzyme coating system will enhance the activity of immobilized glucoamylase.

The amount of coating materials applied must be related to several factors. First, it is desirable to apply a sufficient amount of enzyme and polymer so that the activity of the immobilized enzyme is relatively high. It is desirable that at least 25% by weight of the enzyme coating system be comprised of the enzyme. Good results have been obtained when the enzyme coating solution contains from about 25% to about 35% by weight enzyme. Second, the amount of polymer is relatively small, compared to the amount of enzyme. For the immobilization of glucoamylase, it is desirable that from about 0.1% to about 10.0% by weight of the enzyme coating system be comprised of polyethyleneimine. Preferably, the enzyme coating system will contain from about 0.5% to about 3.0% by weight polyethyleneimine, about 1% being most preferred. Third, the amount of cross-linking agent must be adjusted to achieve a balance of endurance and activity for the enzyme. The amount of cross-linking is controlled by adjusting the concentration of the cross-linking agent in the solution and the amount of solution that is applied. When the embodiments illustrated in the drawings are used, the speed of the applicator roll and other operating parameters may be adjusted to control the amount of cross-linking solution applied. When immobilizing glucoamylase, it is desirable to use a glutaraldehyde solution of from about 0.5% to about 15%, preferably 1.0% to about 10.0%. A solution of about 1.0% to about 1.5% glutaraldehyde is most preferred. Good results were obtained by adding 1 milliliter of a 1% solution of glutaraldehyde per gram of glass. Although a broad range of applicator speeds will yield bundles with effective enzyme activities, the more efficient coatings, i.e., higher enzyme activities, were produced at higher applicator speeds.

The activity of the immobilized enzyme may be contrasted with the activity of the enzyme in the free state. Desirably, the degree of cross-linking is limited so that the activity of the immobilized enzyme is at least 10% of the activity of an equivalent amount of free enzyme, preferably 50%.

The endurance of the immobilized enzyme may be rated in terms of half-life. The half-life is the time the immobilized enzyme may be in contact with a substrate until its activity is reduced by one-half. Usually, half-life is expressed in days. In accordance with the invention, the half-life is at least 2 days, preferably at least 10 days and still more preferably at least 20 days, at a temperature of 60° C.

The following Examples illustrate useful formulations for application of glucoamylase. Unless specified otherwise in these examples, the polyethyleneimine is Polymin P and the enzyme was Diazyme ® L-200, an enzyme solution of 35% by weight solids.

Unless indicated otherwise, the activity of an immobilized enzyme sample was determined by the following method. Approximately one-tenth gram of the coated glass fiber was used as a test sample. The sample was placed in 25 ml of a 10% maltodextrin solution (pH=4.0). The sample was allowed to incubate for 30 minutes in a water bath at 60° C. After 30 minutes, 0.5 ml and 1.0 ml, respectively, of the resultant solution was pipetted into 0.1N KOH. The volume was brought to 10 ml. The solution was mixed and the samples were placed in cups to be tested by the glucose analyzer, the Technicon Auto Analyzer II, to determine the amount of glucose produced. The activity of an enzyme is expressed in terms of units per gram. As used herein, one unit of activity is the amount of enzyme that will produce one micromole of glucose per minute.

In some instances, activities are reported for both the immobilized enzyme composite, i.e., the coating plus glass, as well as for the coating only. The activity of the immobilzed enzyme composite is reported in units per gram and indicates the activity of the total system. The coating activity is reported in units per milligram and reveals the final activity of the enzyme after immobilization. Activities reported only in units/gram, represent the activity of the immobilized enzyme composite. represent the activity of the immobilized enzyme composite. The coating activity divided by the free enzyme activity (34.7 units/milligram) gives an approximate measure of the fraction of enzyme remaining active after immobilization.

EXAMPLE 1

A series of samples of immobilized glucoamylase were made to determine the effect of varying the amount of maltodextrin in the coating solution. The samples consisted of 0.15 grams of E-glass bundles consisting of 170 filaments of 13 micrometer diameter. The samples were soaked for 15 minutes in the enzyme coating solutions having the compositions listed in Table 1 below.

TABLE 1

| Sample No. | Percent** Glucoamylase Solution | Percent* Maltodextrin | Percent* Polyethyleneimine | Immobilized Enzyme Activity (units/gram) | Enzyme Coating Activity (units/milligram) |
|---|---|---|---|---|---|
| 1 | 98 | 0 | 1 | 345 | 29.0 |
| 2 | 96 | 1 | 1 | 359 | 14.7 |
| 3 | 92 | 3 | 1 | 428 | 18.7 |
| 4 | 88 | 5 | 1 | 528 | 18.1 |
| 5 | 84 | 7 | 1 | 260 | 13.4 |
| 6 | 82 | 8 | 1 | 183 | 14.1 |

*Actual percent by weight in the enzyme coating solution.
**An enzyme solution of about 35% solids. The percent enzyme by weight present in the enzyme coating solution of samples 1–6 was about 34, 33, 32, 30, 29 and 28, respectively.
The remaining portion by weight of the enzyme coating solution was essentially water.

After soaking, the bundles were transferred to a screen and allowed to drain for 15 minutes. Then, each bundle was washed with 50 ml of a 14.5% aqueous solution of glutaraldehyde. After 10 minutes, the bundles were washed with 100 ml of distilled water. The bundles were air dried, weighed, and tested for activity. The results are summarized in Table 1 above.

EXAMPLE 2

The following experiments demonstrate the effect of glutaraldehyde concentration on the activity of the enzyme.

A. Glass filament was coated with a mixture containing 5% starch, 1.5% polyethyleneimine and glucoamylase in water. Then samples of the filament were immersed in aqueous solutions containing various amounts of glutaraldehyde. Activities were measured in a manner analogous to that described above, and the results were as follows:

| Glutaraldehyde concentration | 1% | 2% | 3% |
|---|---|---|---|
| Activity (units/gram) | 904 | 590 | 481 |

B. A glass bundle consisting of 2052 filaments of 13 micrometer diameter E-glass (K6.75 strand) was coated with an enzyme solution consisting of 1.5% PEI, 5% starch, and 87% glucoamylase solution Diazyme (L200). One gram of glass was coated with 0.6 milliliters of enzyme solution.

The coated bundles were then cross-linked by adding 0.5 milliliters of 0.5%, 1.0%, or 1.5% aqueous glutaraldehyde solution per gram of glass.

The measured activities of the enzyme were as follows:

| Glutaraldehyde concentration | 0.5% | 1.0% | 1.5% |
|---|---|---|---|
| Immobilized Enzyme Activity (units/gram) | 925 | 1187 | 932 |
| Coating Activity (units/milligram) | 13.5 | 16.5 | 11.4 |

EXAMPLE 3

Samples of glass fiber were coated with an enzyme solution similar to that described in Example 2. Then one gram samples of the enzyme-coated fibers were immersed in measured quantities of a 1% solution of glutaraldehyde. The samples were allowed to stand until all of the measured amount of solution was taken up by the fibers. Then the activities of the samples were measured. The activities were as follows:

| Glutaraldehyde Sample (microliters) | Activity (Units Per Gram) |
|---|---|
| 50 | 874 |
| 100 | 655 |
| 150 | 468 |

EXAMPLE 4

Example 3 was repeated, using a solution which contained 2% polyethyleneimine, with the following result:

| Glutaraldehyde Sample (microliters) | Activity (Units Per Gram) |
|---|---|
| 50 | 597 |
| 100 | 864 |
| 150 | 522 |

EXAMPLE 5

A sample of glass filaments containing 408 filaments per strand was coated in the method of Example 1. The first solution contained 90.5% Diazyme (glucoamylase), 5% starch, 3% hydroxyethyl cellulose, and 1.5% polyethyleneimine. The second solution contained 1% glutaraldehyde. Half-life was measured in a column by exposing the sample to a solution containing 27% of a 10 D.E. maltodextrin and a pH of 4.0. The column contained 40 cc and the flow rate was 0.25 space velocities per hour. The half-life was found to be 40 days, at a temperature of 60° C.

EXAMPLE 6

Half-life was measured on another sample which was coated by a procedure analogous to Example 3. The first coating solution was used in an amount of 0.6 ml per gram of glass and contained 8% Diazyme, 5% starch, calcium chloride and 1.5% polyethyleneimine. The pH was 4.0 and the temperature was 60° C. The first coating was cross-linked by standing for 1 hour with 1.5 ml per gram of glass of a 1% aqueous glutaraldehyde solution. The fibers were tested in a column which contained 6.03 cc and the flow rate was 3.5 space velocities per hour. The half-life was 24 days.

EXAMPLE 7

A sample of glass fibers (K6.75, 2052 filaments per strand) was coated in a manner analagous to Example 6 using 0.6 ml per gram of a solution containing 87% Diazyme L-200, 5% starch and 1.5% polyethyleneimine. The sample was cross-linked by standing for one hour with 0.5 ml per gram of a 1% aqueous glutaraldehyde solution, at a temperature of 60° C. It was found to have a 15 day half-life.

EXAMPLE 8

A paste was made by stirring sufficient hydrolyzed starch (10 D.E. maltodextrose) with water to provide a concentration of 50% hydrolyzed starch. A solution was made by adding the following to water to form about 2,000 grams of treating liquid:

|  | Dry solids (grams) |
| --- | --- |
| Glucoamylase | 31.1 |
| Polymin P | 1.5 |
| Hydroxyethyl cellulose | 2.0 |
| Starch paste | 3.0 |
| Calcium chloride | 0.005 |

This liquid was applied to E-glass filaments of diameter 13 microns, using the procedure illustrated in FIG. 2. With a wet pick-up of 20%, and using a 7% aqueous glutaraldehyde solution, the product was found to have an activity of 1,200 to 1,800 units per gram.

EXAMPLE 9

One gram samples were cut from a bundle consisting of 2052 filaments of 13 micron E-glass (K6.75). Each sample was coated with 0.6 milliliter of one of the enzyme solutions described in Table 2.

TABLE 2

| Sample No. | Percent Polyethylene imine | Percent Maltodextrin | Percent Glucoamylase Solution | Percent Glutaraldehyde | Immobilizd Enzyme Activity (units/gram) | Enzyme Coating Activity (units/milligram) |
| --- | --- | --- | --- | --- | --- | --- |
| 1 | 1.0 | 5 | 88 | 1.0 | 793 | 9.0 |
| 2 | 1.5 | 5 | 87 | 1.0 | 847 | 9.3 |
| 3 | 2.0 | 5 | 86 | 1.0 | 865 | 7.6 |
| 4 | 2.5 | 5 | 85 | 1.0 | 749 | 4.6 |
| 5 | 1.0 | 5 | 88 | 14.5 | 293 | 5.2 |
| 6 | 1.5 | 5 | 87 | 14.5 | 263 | 4.7 |
| 7 | 2.0 | 5 | 86 | 14.5 | 301 | 3.8 |
| 8 | 2.5 | 5 | 85 | 14.5 | 201 | 1.4 |

Each coated sample was then treated with 1.0 milliliter of an aqueous glutaraldehyde solution per gram of glass. Two sets of samples were treated; one set was treated with a solution containing about 1% glutaraldehyde and the other set was treated with a solution containing about 15% glutaraldehyde.

The results are summarized in Table 2 above. It can be seen that the activity of the immobilized enzyme was effected by the degree of cross-linking, and that the activity was higher when the cross-linking agent was more dilute, i.e., a 1% solution of glutaraldehyde. Secondly, it can be seen that the activity was influenced by the amount of polyethyleneimine; the highest activity was achieved with 2% polyethyleneimine. The highest efficiency was achieved with 1.5% polyethyleneimine.

EXAMPLE 10

One gram samples were cut from a glass strand consisting of 2052 filaments of 13 micrometer diameter E-glass. Each of the samples were coated with 0.6 milliliters of one of the solutions described in Table 3.

TABLE 3

| Percent Polyethylene imine | Percent Maltodextrose | Percent Glucoamylase Solution | Percent Calcium Chloride | Immobilized Enzyme Activity (units/gram) | Enzyme Coating Activity (units/milligram) |
| --- | --- | --- | --- | --- | --- |
| 1.5 | 5.0 | 87.0 | 0.0 | 832 | 8.9 |
| 1.5 | 5.0 | 86.4 | 0.04 | 972 | 29.5 |

The coated strands were treated with 1 milliliter of 1.0% aqueous glutaraldehyde solution per gram of glass, and the activities of the strands and the coatings are given in Table 3. The data demonstrates the advantage of adding calcium chloride to the coating solution.

EXAMPLE 11

The following experiments demonstrated the use of different polymers and cross-linking agents.

A. One gram samples were cut from a glass strand consisting of 2052 filaments of 13 micrometer diameter E-glass. Each sample was coated with 0.6 milliliter of an aqueous enzyme solution containing 1.0% polyethyleneimine, 5% maltrodextrose and 88% glucoamylase solution (L200). Samples were then cross-linked with one ml of an aqueous solution of one of the following, per gram of glass, and had the activities summarized in Table 4 below:

TABLE 4

| Percent Cross-linking Agent | Immobilized Enzyme Activity (units/gram) | Enzyme Coating Activity (units/milligram) |
| --- | --- | --- |
| 4% toluene 2,4 diisocyanate | 1217 | 6.86 |
| 5% oxirane | 1416 | 19.40 |

B. A glass bundle consisting of 2052 filaments of 13 micrometer diameter E-glass was coated by soaking the bundle in a solution containing 10% polyethyleneimine and 90% glucoamylase solution. The bundle was placed on a screen and allowed to drain for 15 minutes.

The bundle was then cross-linked by dipping it for 15 minutes in an aqueous solution of 10% divinyl sulfone. Then it was washed with water. The activity of the coated bundle was 928 units per gram; the activity of the coating itself was 4.8 units per milligram.

C. Using the method described in B above, a glass bundle was coated with a solution consisting of 30% polyvinylalcohol of molecular weight 86,000 and 70% glucoamylase solution. The bundle then was cross-linked for 30 minutes at 50° C. with 4% toluene diisocyanate, using the method described in B above. The resulting immobilized enzyme composite had an activity of 1,235 units per gram. The activity of the coating was 2.9 units per milligram.

EXAMPLE 12

A glass bundle consisting of 408 filaments of 9 micrometer diameter E-glass (G75 strand) was coated with two successive kiss rollers using the apparatus illustrated in FIG. 1. The first applicator contained the aqueous enzyme coating solution. The coating solution consisted of 1.5% polyethyleneimine, 5% maltodextrin, 2% hydroxyethyl-cellulose and 85% glucoamylase solution. The applicator roll speed was varied from 20 to 190 rpm to vary the quantity of enzyme solution coated onto the strand.

The second applicator contained a 1% aqueous glutaraldehyde solution. Its speed also was varied between 20 and 190 rpm, to vary the amount of cross-linking agent added to the bundle.

Figure 3:
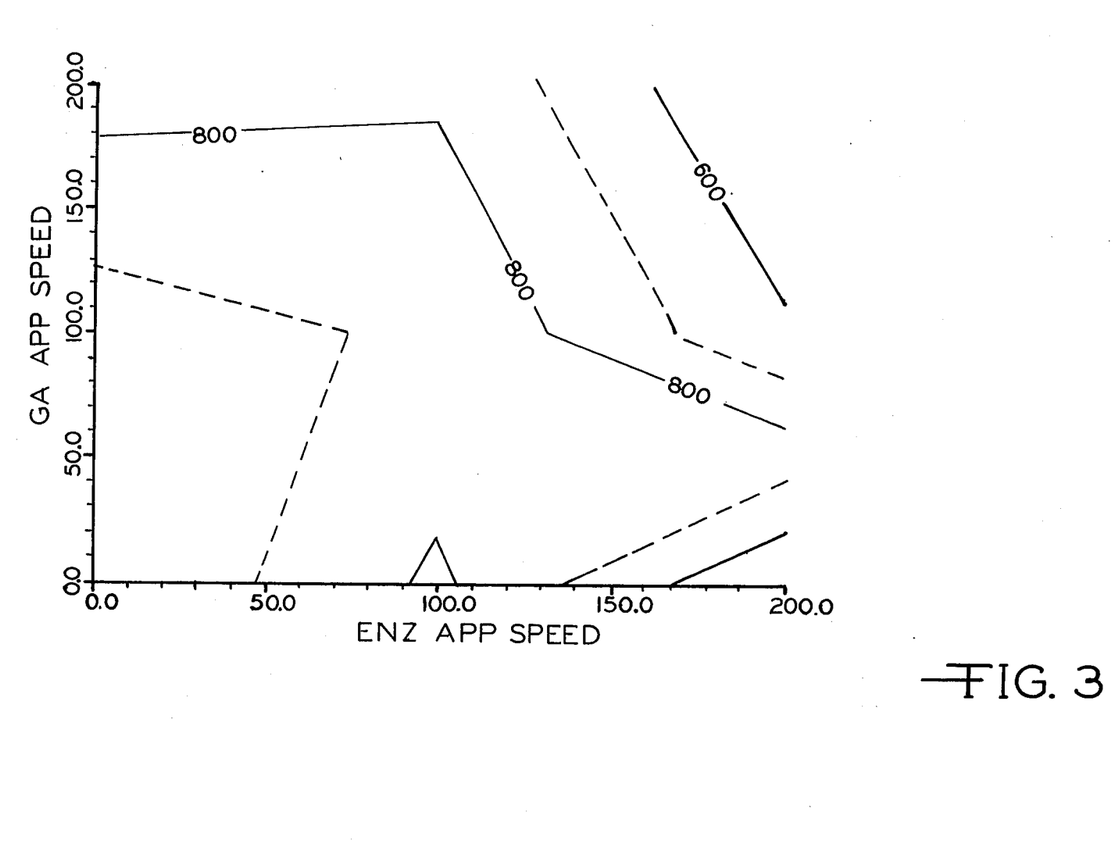
FIG. 3 is a contour map of the activity of a coated bundle of glass filaments as a function of the speed of the applicators which apply the enzyme coating system and the cross-linking agent.
Figure 4:
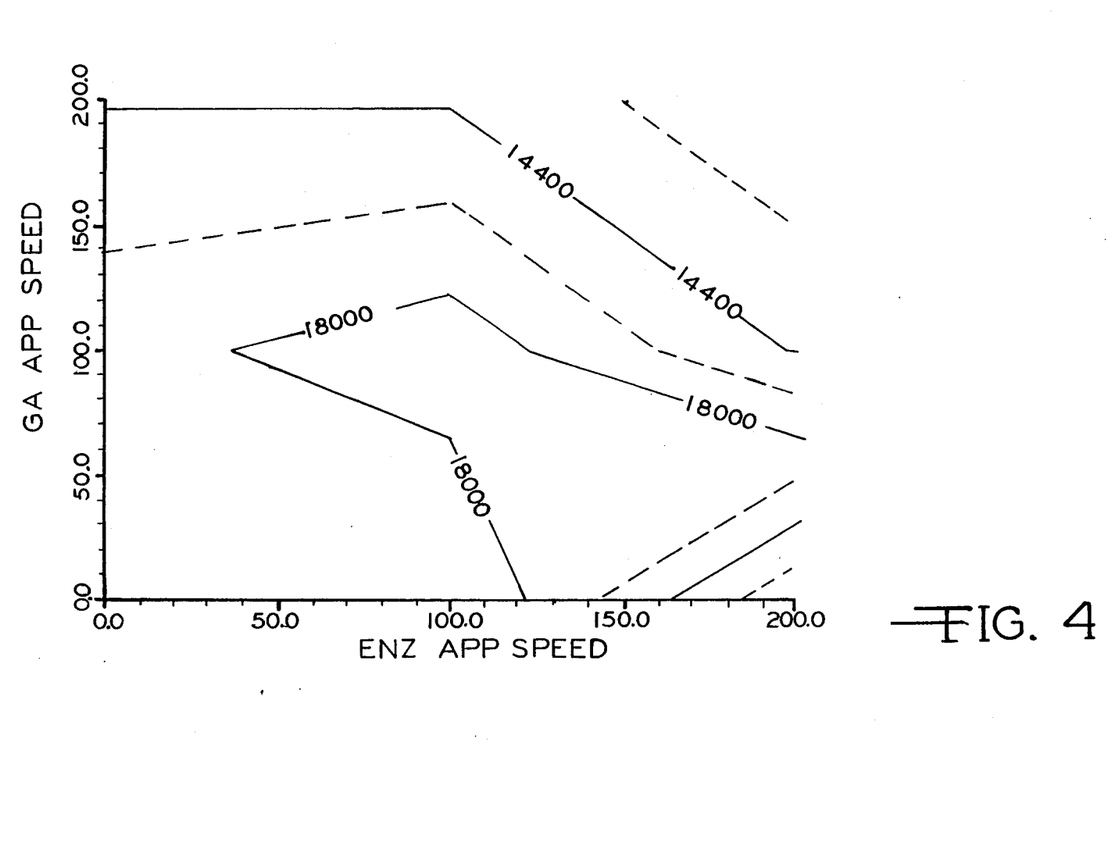
FIG. 4 is a contour map of the activity of a coated bundle of glass filament per unit weight of the coating as a function of the applicator speeds.

The coated bundles were air dried for one hour, washed with water and tested for activity. The activities of the samples are recorded as a function of both applicator speeds in a graph in FIG. 3. FIG. 3 reads as a contour map of equal activities (units per gram). For example, the line labeled 800 denotes those applicator speeds which will produce a strand whose activity is 800 units per gram. In a similar manner, FIG. 4 records the activities of the coatings as a function of applicator speeds. It demonstrates that in general more efficient coatings are produced at higher applicator speeds.

EXAMPLE 13

A G75 glass bundle was coated with a solution consisting of 87% enzyme solution, 5% maltodextrin and 1.5% polyethyleneimine. Each gram of glass was coated with 0.6 ml of solution. The coating was cross-linked with 1% aqueous glutaraldehyde solution, using 0.5 ml of solution per gram of glass. Ten grams of glass bundle were packed into a column; the bed volume of the bundle was 18.5 cm³. Five hundred milliliters of a 27% 10 D.E. maltodextrin solution was recycled through the column at a flow rate of 185 cm³ per hour.

Table 5 lists the percent of starch converted into glucose in this procedure. It will be seen that over 94.7% of the starch was converted to glucose.

TABLE 5

| Time (Hours) | % Conversion |
| --- | --- |
| 2 | 18.19 |
| 3 | 20.95 |
| 4 | 26.64 |
| 5 | 36.76 |
| 6 | 39.14 |
| 7 | 42.37 |
| 24 | 79.90 |
| 27 | 82.18 |
| 46.5 | 90.16 |
| 78.5 | 93.35 |
| 96 | 93.88 |
| 103.5 | 94.21 |
| 119.5 | 94.33 |
| 124.5 | 94.46 |
| 127.5 | 94.47 |
| 143.5 | 94.58 |
| 147.5 | 94.60 |
| 151.5 | 94.61 |
| 167.5 | 94.46 |
| 172.5 | 94.45 |
| 175.5 | 94.56 |
| 191.5 | 94.49 |
| 195.5 | 94.64 |
| 199.5 | 94.74 |
| 242.5 | 94.72 |
| 264.5 | 94.77 |
| 268 | 94.52 |

Although the invention has been described in terms of specific embodiments of a manner in which the invention may be practiced, this is by way of illustration only and the invention is not necessarily limited thereto since alternative embodiments and operating techniques will become apparent to those skilled in the art. Accordingly, modifications are contemplated which can be made without departing from the spirit of the described invention.

We claim:

1. A method for forming an immobilized enzyme composite comprising:
   coating an unsized non-porous glass fiber with an enzyme coating solution containing an enzyme and a soluble polymer, contacting said coated fiber with a cross-linking agent which is effective to insolubilize said polymer and immobilize said enzyme, the amount of said agent being controlled such that the immobilzed enzyme has an activity of at least 10% of its activity in the free state.

2. The method of claim 1 wherein said non-porous fiber is a continuous fiber and is coated by contact with a roller.

3. The method of claim 1 wherein said fiber is a continuous fiber and said coating is done by immersing said fiber in said coating solution and passing said coated fibers through a stripper die.

4. The process of claim 1 wherein said coating solution includes a substrate for said enzyme.

5. The process of claim 1 and further including the step of draining excess coating from said coated glass fiber prior to contacting with said cross-linking agent.

6. The process of claim 1 wherein the amount of said agent is controlled such that the immobilized enzyme has an activity of at least 50% of its activity in the free state.

7. The process of claim 1 wherein said agent is controlled such that the endurance of the immobilized enzyme, as determined by half-life, is at least two days.

8. The process of claim 7 wherein said endurance is at least ten days.

9. The process of claim 7 wherein said endurance is at least 20 days.

10. The process of claim 1 wherein said process is continuous and said polymer is a polyalkyleneimine.

11. The process of claim 1 wherein said coating and said contacting is controlled so that said insolubilized polymer is porous to a substrate for said enzyme.

12. The process of claim 1 wherein said polymer is polyethyleneimine.

13. The process of claim 12 wherein said enzyme is an amylase.

14. The process of claim 13 wherein said amylase is glucoamylase.

15. The process of claim 14 wherein said cross-linking agent is glutaraldehyde.

16. The process of claim 4 wherein said substrate is maltodextrin.

17. The process of claim 1 wherein said enzyme coating solution includes $CaCl_2$.

18. The process of claim 11 wherein said coating solution includes a cellulose ether thickener.

19. The process of claim 15 wherein said contacting is done with an aqueous glutaraldehyde solution containing from 0.5% to 1.5% by weight of said glutaraldehyde.

20. The process of claim 19 wherein said solution contains about 1% glutaraldehyde.

21. The process of claim 1 wherein said coating solution contains at least about 25% by weight of enzyme and about 0.5% to about 3% by weight polymer.

22. The process of claim 21 wherein said solution further contains about 1% to about 5% by weight enzyme substrate.

23. The product of the process of claim 1.

24. The product of claim 23 wherein the composite has an activity of 183 units per gram.

25. The product of the process of claim 3 wherein said composite has an activity of 1200–1800 units per gram.

26. A continuous process for forming an immobilized enzyme composite comprising, in a continuous flow, supplying an unsized non-porous continuous glass fiber to a first station, coating said glass fiber at said first station with a coating solution containing an enzyme and a soluble polymer, moving said coated continuous fiber to a second station and applying a cross-linking agent to said coated fiber at said second station, the amount of cross-linking agent being controlled to be effective to insolubilize said polymer and immobilize said enzyme so that said immobilized enzyme has an activity of at least 10% of its activity in the free state.

* * * * *